(12) United States Patent
Navab

(10) Patent No.: US 11,045,090 B2
(45) Date of Patent: Jun. 29, 2021

(54) APPARATUS AND METHOD FOR AUGMENTED VISUALIZATION EMPLOYING X-RAY AND OPTICAL DATA

(71) Applicant: Technische Universität München, Munich (DE)

(72) Inventor: Nassir Navab, Munich (DE)

(73) Assignee: Technische Universität München, Munich (DE)

( * ) Notice: Subject to any disclaimer, the term of this patent is extended or adjusted under 35 U.S.C. 154(b) by 5 days.

(21) Appl. No.: 15/763,966

(22) PCT Filed: Sep. 28, 2016

(86) PCT No.: PCT/EP2016/073113

§ 371 (c)(1),
(2) Date: Mar. 28, 2018

(87) PCT Pub. No.: WO2017/055352

PCT Pub. Date: Apr. 6, 2017

(65) Prior Publication Data

US 2018/0279883 A1 Oct. 4, 2018

(30) Foreign Application Priority Data

Sep. 29, 2015 (EP) ..................................... 15187466

(51) Int. Cl.
*A61B 5/0432* (2006.01)
*A61B 5/00* (2006.01)
(Continued)

(52) U.S. Cl.
CPC .......... *A61B 5/0035* (2013.01); *A61B 5/0073* (2013.01); *A61B 5/0077* (2013.01);
(Continued)

(58) Field of Classification Search
CPC ...... A61B 6/4258; G01N 23/04; G01N 23/06; G01N 23/083
See application file for complete search history.

(56) References Cited

U.S. PATENT DOCUMENTS 5,923,727 A 7/1999 Navab
2003/0082104 A1 5/2003 Mertelmeier
(Continued)

FOREIGN PATENT DOCUMENTS

WO WO2014206760 12/2014

OTHER PUBLICATIONS

European Search Report for European Patent Application No. 15187466, dated Mar. 22, 2016, 7 pages.
(Continued)

*Primary Examiner* — David P Porta
*Assistant Examiner* — Mamadou Faye
(74) *Attorney, Agent, or Firm* — Dority & Manning, P.A.

(57) ABSTRACT

A medical imaging apparatus for combined X-ray and optical visualization is provided. It comprises: an X-ray detector positioned above a patient; an X-ray source positioned below a patient; a control device; and a camera setup adapted to deliver an optical stereoscopic or 3D image. Thereby, the camera setup is positioned adjacent to the X-ray detector above the patient, and the control device is adapted to calculate an optical 2D image or a 3D surface from the data delivered by the camera setup, that optical 2D image or 3D surface having a virtual viewpoint similar to the viewpoint of the X-ray source. It is further adapted to superimpose an X-ray image acquired by the X-ray detector and the optical 2D image or 3D surface in order to achieve an augmented optical/X-ray image.

13 Claims, 4 Drawing Sheets

(51) Int. Cl.
*A61B 6/00* (2006.01)
*A61B 6/03* (2006.01)
(52) U.S. Cl.
CPC .............. *A61B 6/03* (2013.01); *A61B 6/4441* (2013.01); *A61B 6/5247* (2013.01)

(56) References Cited

U.S. PATENT DOCUMENTS

| | | | |
|---|---|---|---|
| 2007/0238957 | A1 | 10/2007 | Yared |
| 2010/0266171 | A1* | 10/2010 | Wendler .................. G01T 1/161 |
| | | | 382/128 |
| 2015/0272694 | A1* | 10/2015 | Charles .................. A61B 90/37 |
| | | | 600/202 |
| 2016/0249984 | A1* | 9/2016 | Janssen .................... A61B 6/04 |
| | | | 600/427 |
| 2017/0215823 | A1* | 8/2017 | Ivanov .................... A61B 90/37 |
| 2019/0043612 | A1* | 2/2019 | De Cock ............... G06F 19/321 |

OTHER PUBLICATIONS

International Search Report and Opinion for PCT/EP2016/073113, dated Dec. 9, 2016, 12 pages.

* cited by examiner

11,045,090 B2

APPARATUS AND METHOD FOR AUGMENTED VISUALIZATION EMPLOYING X-RAY AND OPTICAL DATA

CROSS REFERENCE TO RELATED APPLICATIONS

This application is the U.S. National Stage entry of International Application Number PCT/EP2016/073113 filed under the Patent Cooperation Treaty having a filing date of Sep. 28, 2016, which claims priority to European Patent Application Number 15187466.6 having a filing date of Sep. 29, 2015, which are incorporated herein by reference.

TECHNICAL FIELD

The present disclosure relates to imaging systems. More particularly, it relates to a device and method for the imaging of a body, in particular a human body, for medical purposes. Even more particularly, it relates to an apparatus and method for augmenting optical images with X-ray images.

BACKGROUND OF THE INVENTION

In addition to X-ray images of an object, it is often useful to have a corresponding video image. If the two could be combined into a composite image, then one could immediately see how the features revealed by the X-ray relate to the surface features displayed in a video image.

One method of correlating a video image with an X-ray image of the same object is by acquiring the respective images from the same point in space. To this end, a video or optical camera can be placed at a point in space equivalent to that of the X-ray source—by deflecting a portion of the optical image with an X-ray transparent mirror. Such techniques are disclosed in, for example, U.S. Pat. Nos. 6,473,489 B2, 6,227,704 B1, 6,229,873 B1, 6,447,163 B1, and 7,198,404 B2.

Some of the disclosures above include that the camera is oriented by an alignment procedure, for example using a laser, to ensure that it is located at a point optically equivalent to the location of the X-ray source. Superimposition can then be achieved by warping one image onto the other. However, all of these methods reduce the working space below the X-ray source due to the employed mirror, which is particularly significant when the method is employed in an operating room (OR). In this case, space for the movement of surgeons is reduced.

In view of the above, there is a need for the present invention.

SUMMARY OF THE INVENTION

The problems mentioned above are at least partly solved by a medical imaging apparatus according to claim 1, and a visualization method using X-ray and optical information according to claim 8.

In a first aspect, a medical imaging apparatus for combined X-ray and optical visualization is provided. It comprises: an X-ray detector positioned above a patient; an X-ray source positioned below a patient; a control device; and a camera setup adapted to deliver an optical stereoscopic or 3D image. Thereby, the camera setup is positioned adjacent to the X-ray detector above the patient, and the control device is adapted to calculate an optical 2D image or a 3D surface from the data delivered by the camera setup, that optical 2D image or 3D surface having a virtual viewpoint similar to the viewpoint of the X-ray source. It is further adapted to superimpose an X-ray image acquired by the X-ray detector and the optical 2D image or 3D surface in order to achieve an augmented optical/X-ray image.

In a second aspect, a visualization method using X-ray and optical information is provided. It comprises: obtaining an X-ray image with an X-ray source positioned below a patient and an X-ray detector positioned above a patient; calculating an optical 2D image or a 3D surface from data delivered by the camera setup, wherein the camera setup is positioned adjacent to the X-ray detector above the patient; and calculating an augmented 2D optical/X-ray image from the X-ray image and the 3D surface or the optical 2D image, wherein that optical 2D image or 3D surface have a virtual viewpoint similar to the viewpoint of the X-ray source.

Further aspects, advantages and features of the present invention are apparent from the dependent claims, the description and the accompanying drawings.

BRIEF DESCRIPTION OF THE DRAWINGS

A full and enabling disclosure, including the best mode thereof, to one of ordinary skill in the art is set forth more particularly in the remainder of the specification, including reference to the accompanying figures wherein.

DETAILED DESCRIPTION OF THE INVENTION

Figure 1:
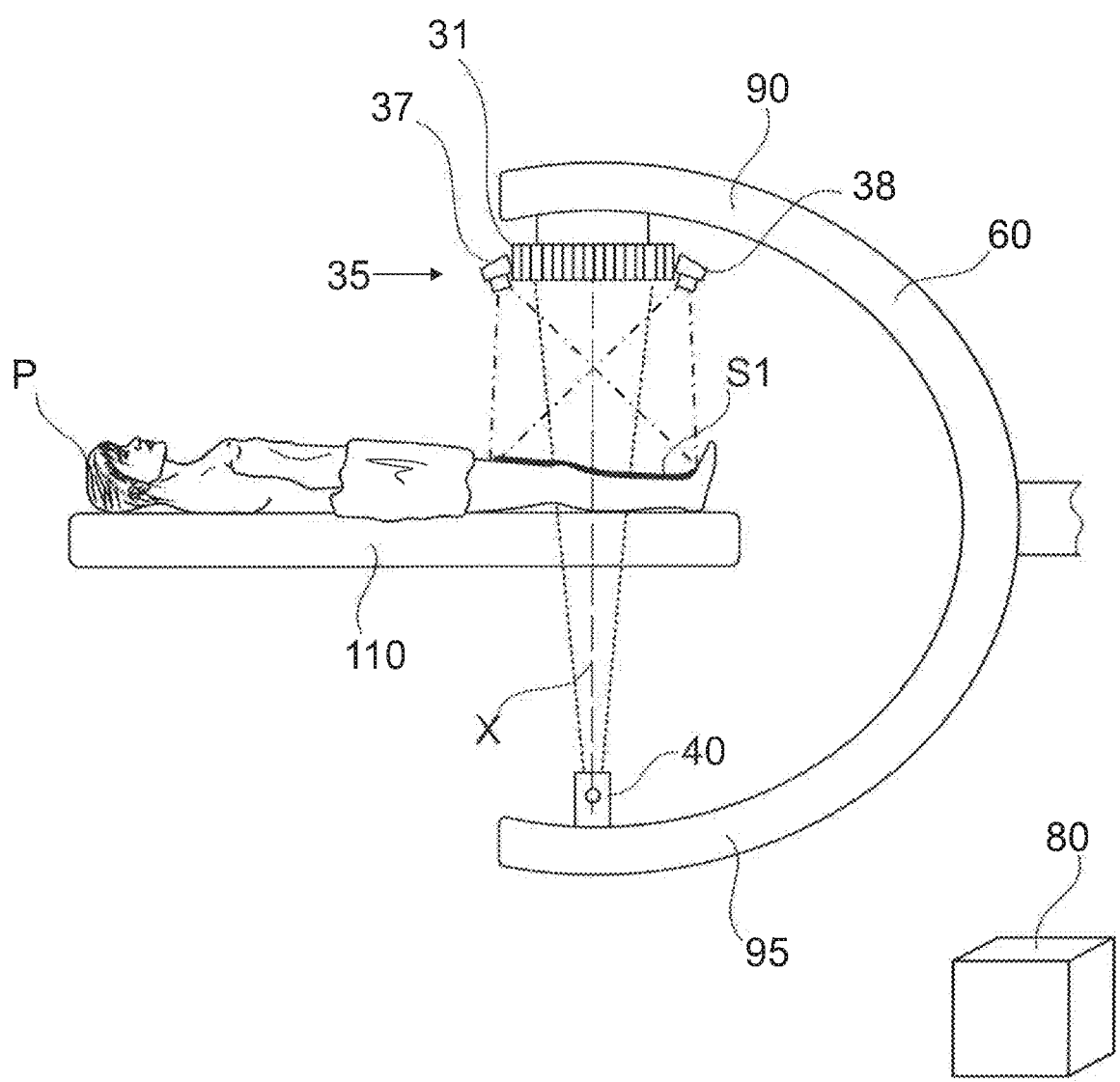
FIG. 1 schematically shows a perspective view of a diagnostic device according to embodiments.

Reference will now be made in detail to various embodiments, one or more examples of which are illustrated in each figure. Each example is provided by way of explanation and is not meant as a limitation. For example, features illustrated or described as part of one embodiment can be used on or in conjunction with other embodiments to yield yet further embodiments. It is intended that the present disclosure includes such modifications and variations.

Within the following description of the drawings, the same reference numbers refer to the same components. Generally, only the differences with respect to the individual embodiments are described. When several identical items or parts appear in a figure, not all of the parts have reference numerals in order to simplify the appearance.

The systems and methods described herein are not limited to the specific embodiments described, but rather, components of the systems and/or steps of the methods may be utilized independently and separately from other components and/or steps described herein. Rather, the exemplary embodiment can be implemented and used in connection with many other applications, in particular with other medical diagnostic or treatment methods than the ones exemplarily shown.

Although specific features of various embodiments of the invention may be shown in some drawings and not in others, this is for convenience only. In accordance with the principles of the invention, any feature of a drawing may be referenced and/or claimed in combination with any feature of any other drawing.

As used herein, the term "3D camera" is used interchangeably with "RGB-D camera" and is intended to mean a video camera device which provides depth information (as a function of a distance from the camera) in addition to a color or grayscale image. Thus, it can capture RGB images along with depth information. RGB-D cameras usually rely on either active stereo imaging or time-of-flight sensing to generate depth estimations at every pixel. Thus, 3D reconstruction of the object(s) in the field of view of the camera in real time is feasible. Since a few years, such RGB-D cameras are available in a small form factor, most prominently have been the inexpensive RGB-D cameras in the gaming domain, such as Kinect by Microsoft. These may be placed suitably above a surgical workspace, where they do not disturb the operations of the surgeon. Alignment of the optical axis of the camera is not required with this technology, since 3D information can be observed from any point of view without distortion, in contradiction to conventional 2D information.

Generally, it is implied that cameras and detectors used herein are connected to a control unit via cable or a wireless connection, while the connections are not explicitly shown in the drawings. Further, it is generally valid that in embodiments X-ray images taken or obtained by an X-ray detector are produced simultaneously or quasi-simultaneously with the optical images of the camera setup, having a delay between them in the order of a few seconds as an upper limit, unless purposefully controlled differently. For example, there may be a delay due to different time spans between optical and X-ray image processing. In particular, all images involved, X-ray or optical, are obtained while the X-ray detector, the camera setup and the X-ray source are all at their fixed positions, and they are kept stationary during imaging. Moreover, the full functionality of the imaging and methods disclosed herein is obtained with the X-ray detector, X-ray source and the optical camera setup being stationary and not moving during an imaging process. This is particularly advantageous when employed during surgery, as the apparatus can be used without interfering with a surgeon's hands and instruments. As used herein, the terms "above" a patient and "below" a patient are intended to mean that the respective item is provided in a hemisphere above the body region to be imaged, or in a hemisphere below the body region to be imaged. Typically, the X-ray source and the X-ray detector are connected by an imaginary line on which the imaged body region is positioned. Unless otherwise stated, this line is typically substantially perpendicular in embodiments described herein, with a tolerance of about 15 degrees. Further, the term "adjacent", as used herein, typically means that the two adjacent-lying items are positioned directly beside each other, either in contact, with a very small gap between them, or with a distance of up to about 20 cm, more typically up to 10 cm, between their outer surfaces.

FIG. 1 shows a medical imaging apparatus 5 for combined X-ray and optical visualization. It comprises an X-ray detector 31 and an X-ray source 40, which are provided opposite to each other and have a common axis X. Between them, an object to be examined or visualized—here the patient P—can be provided. A camera setup 35 is positioned adjacent to the X-ray detector 31. The camera setup 35 is adapted to deliver a 3D image of the patient P. To this end, it typically comprises two RGB-D cameras 37, 38 provided on opposite sides adjacent to the X-ray detector 31. Further, a control device 80 is part of the apparatus. It is adapted to calculate a 3D surface of the patient P from the data delivered by the camera setup 35. The control unit then superimposes an X-ray image acquired by the X-ray detector 31, and the calculated 3D surface. As a result, an augmented optical/X-ray image is achieved.

Thereby, the calculation is carried out such that the 3D surface is calculated with a virtual viewpoint similar to the viewpoint from the X-ray source 40. FIG. 1, as the source is provided below the patient P to be examined, here a patient P on a bed 110. Hence, the X-ray source is provided below the patient P on the bed 110. This configuration is often preferred by medical personnel, as scattered X-ray radiation from the body of patient P is mainly directed backwards, which in this configuration means downwards, minimizing radiation exposure of the upper body parts of medical personnel in the surroundings of bed 110, for example during surgery. It is understood that the embodiments herein may also be realized with an X-ray source above the bed, with the camera setup adjacent to it.

In the following, a method for augmenting an X-ray image taken by the X-ray detector 31 with optical data, derived from the camera setup 35, is provided. Thereby, in the following the camera setup comprises two 3D cameras 37, 38, as shown in FIG. 1. Further below, it is described that in embodiments, also other configurations are possible for the camera setup 35. As the X-ray source is, in the configuration described with respect to FIG. 1, below the patient P, and below the bed 110, the viewpoint of the X-ray image is also from below. Thus, in order to achieve an augmented image which resembles the correct spatial order and appearance of the plurality of objects to be included—namely the bone structure of the X-ray image and the outer surfaces of the body of the patient P, being the "optical component" derived from the RGB-D data of the camera setup 35—there is the challenge that from a viewpoint of the X-ray source 40 below the bed 110, the 3D surface of the body of the patient P has to be shown from a viewpoint below the body. However, the available data is only taken by the camera setup from above the patient P.

Hence, the 3D surface S1 of the upper side of the patient's body is taken—by the control unit 80—as a point cloud in 3 dimensions, and a new view on it is calculated from below, that is, in two dimensions from the viewpoint of the X-ray source 40. This surface image S2, which is equivalent to a look from the inside of the body of the patient P to the upper surface S1, is typically shaded. Thereby, virtual light source(s) may be provided at the location of the X-ray source or in its vicinity, in order to achieve an optical result which comes close to an impression as if the viewer would really look on that body surface S1 from below. As a texture or shading colour, colours of the skin may—just as a non-limiting example—be chosen. The shading method is inspired by the presentation modality of depth. The RGB-D cameras used contain a depth camera which can measure depth and store it in an image. People usually show depth or depth image as a grey image, in which the near objects are bright and the far is dark. This obeys the "dark-is-deep" rule and it can provide people the spatial relationship of the scene. As is known, the projection of a 3D scene to a 2D image reduces one dimension—the z dimension. With the depth information presenting by another form—color, the viewer can obtain the 3D position of every pixel in the 2D image.

The X-ray picture in 2D of the body of the patient P lies, from a viewpoint of the X-ray-source 40, below the surface S1 of patient P. Hence, the X-ray image is positioned in front of the calculated 2D image of surface S1 for the rendering process which yields the combined 2D image of the upper body surface S1 and the 2D X-ray image.

An exemplary result for a calculation as described before is shown in FIG. 2. Thereby, a hand is the object which is placed between X-ray-source 40 and X-ray detector 31 (located in the foreground), with the palm of the hand directing upwards to the X-ray detector 31 (located in the background). Additionally, an elliptical alpha-blending is employed to display a part of the X-ray image. The size and position of this elliptical-shaped filter 102 may also be changed by an operator, for example.

In embodiments, the two 3D cameras 37, 38 in FIG. 1 may be replaced by two 2D cameras 41, 42, wherein the surface S1 is calculated from the stereoscopic view of the two 2D cameras. Also, the camera setup may comprise only one 3D camera 37. In this case, the quality of the surface is smaller than in the described case with two 3D cameras 37, 38.

Figure 2:
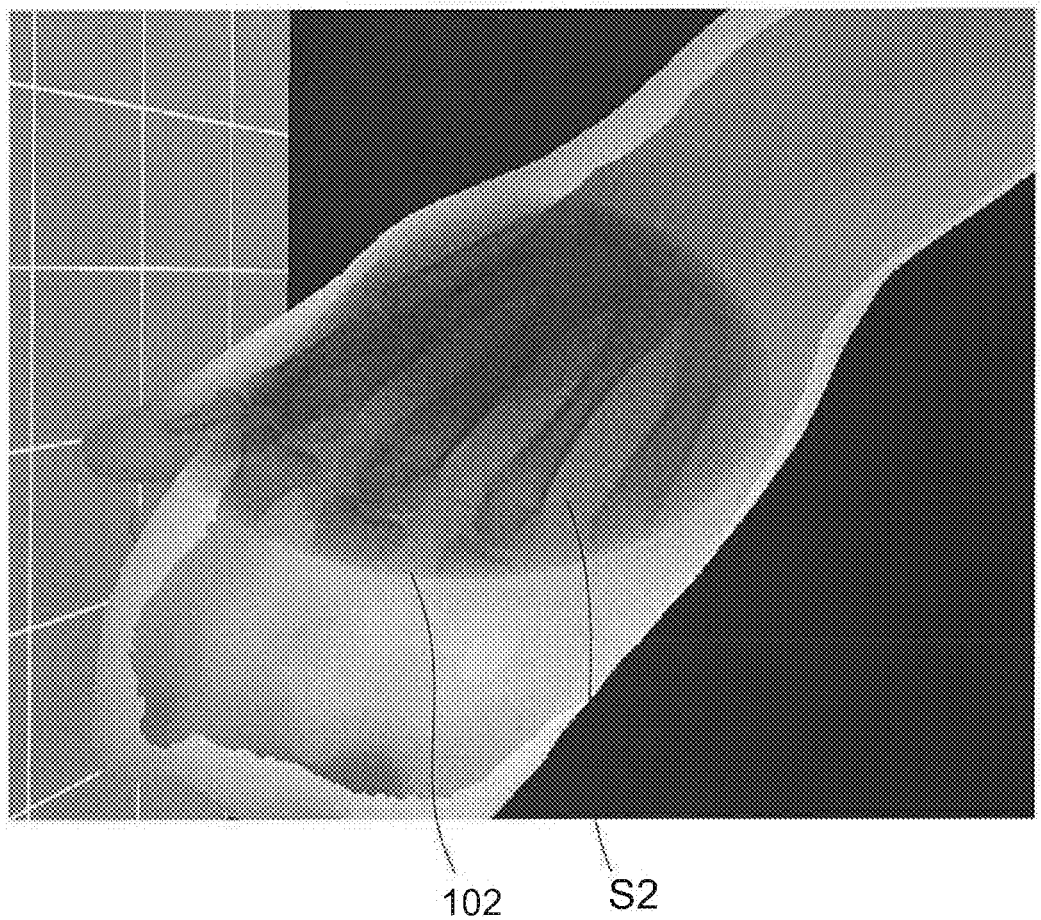
FIG. 2 schematically shows a visualization with a diagnostic device according to embodiments.
Figure 3:
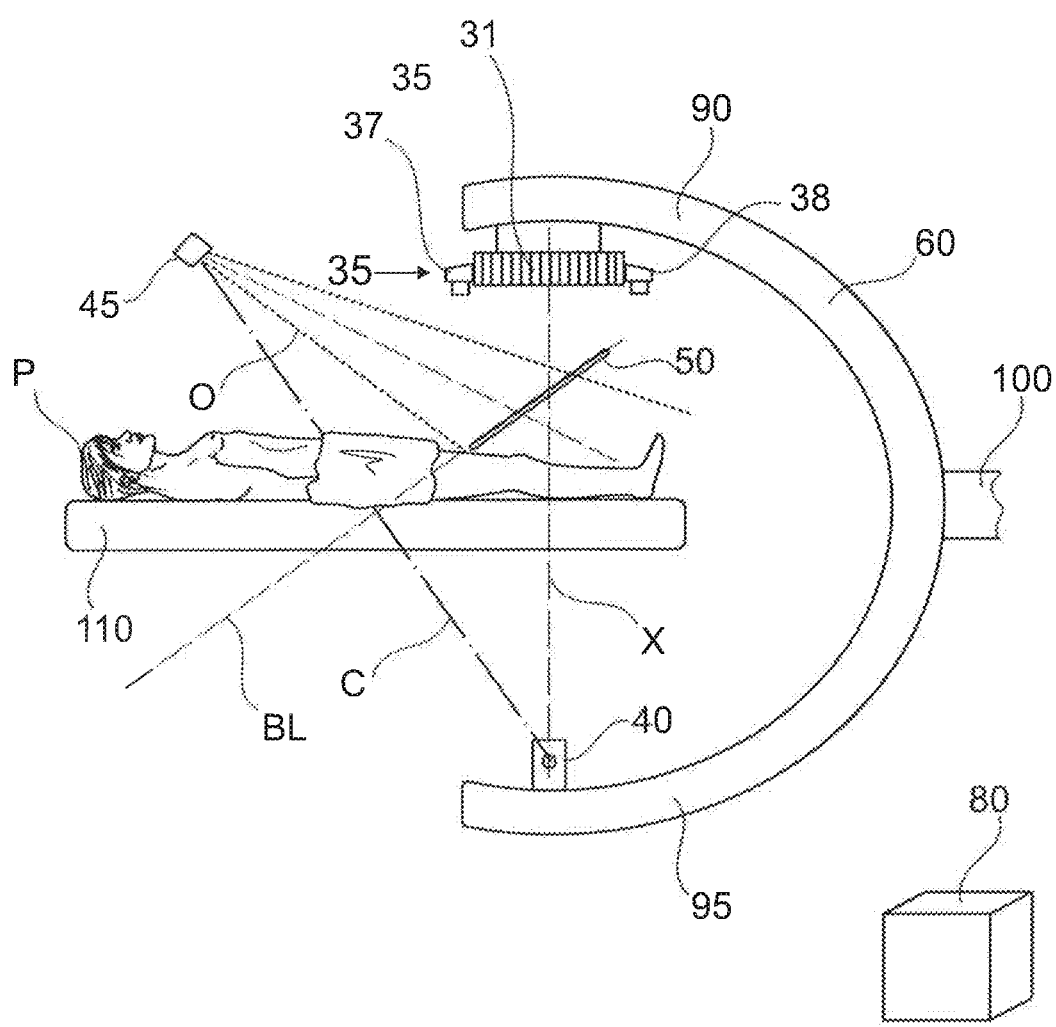
FIG. 3 schematically shows a perspective view of a diagnostic device according to further embodiments.

The above shown method and visualization according to embodiments serves for displaying an augmented optical/X-ray-image from the viewpoint of an X-ray source 40 below a patient bed 110, carried out with an apparatus as shown in FIG. 1, to obtain a visualization as shown in FIG. 2. In an embodiment based on the apparatus and visualization method as just described, a further, side visualization channel is introduced with the apparatus as described with respect to FIG. 3. To this end, a further camera is provided on the side. This side 2D or 3D camera 45 is positioned to provide a side view on an area above the object or patient P to be examined. Thereby, typically the hands of a surgeon and an employed surgical instrument are visualized. The optical axis O of the side 2D or 3D camera 45 has an angle of about 20 to 160 degrees with respect to an axis X between the X-ray source 40 and the X-ray detector 31. Thereby, a (virtual, non-physical) visual mirror 50 is positioned on the bicentrical line BL which is perpendicular to and extends through the midpoint of the connection C of the position of the X-ray source and that of the side 2D or 3D camera 45 optical center.

The side 2D or 3D camera 45 delivers its data to the control unit 80. The control unit is adapted to calculate a 2D side image based on that data. It thereby calculates a virtual projection of the side image on a plane 110. This plane 110 may typically be displayed together with the augmented visualization of FIG. 2. At the same time, objects just above the patient—meaning just above the surface S1—are also in the field of view of the camera setup 35 and are part of the data provided by the camera setup 35 to the control unit 80. In practice, it is typically distinguished between the recording of the patient P, yielding a first layer, and a second layer including the surgeon's hands and instruments used. While the first layer is blended with the X-ray data as described with respect to FIG. 1 and FIG. 2, the second layer is blended separately into the latter image by a separate alpha-blending process.

Figure 4:
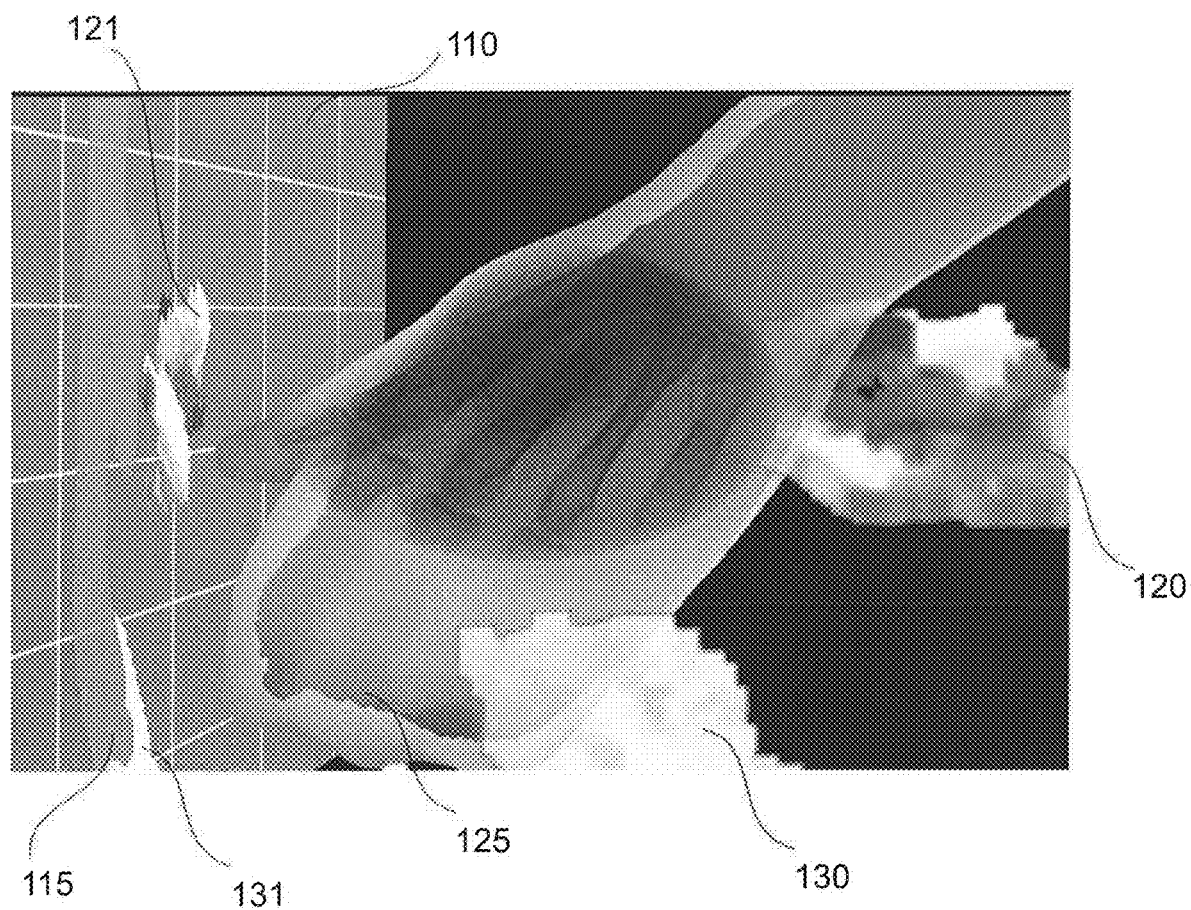
FIG. 4 schematically shows a visualization with the diagnostic device of FIG. 3.

In FIG. 4, the hands 120, 130 of the surgeon are shown in the perspective from the X-ray source below the bed 110, hence they are optically perceived in the image behind the augmented image of the hand 125. Leftwards from the augmented image of the hand 125, the plane 110 with orthographic projections 121, 131 of the surgeon's hands are seen, and with a virtual orthographic projection 115 of the 3D image of the patient hand. In an augmented image with a side view from a side camera 45 as described, the plane 110 with the projections is instead replaced by a virtual screen (visual mirror VM) showing the perspective of the side camera 45.

According to an embodiment, a medical imaging apparatus 5 for combined X-ray and optical visualization is provided. It comprises an X-ray detector 31, an X-ray source 40, a control device 80, and a camera setup 35 adapted to deliver an optical stereoscopic or 3D image, wherein the camera setup 35 is positioned adjacent to the X-ray source 40 or the X-ray detector 31 The control device 80 is adapted to calculate an optical 2D image or a 3D surface from the data delivered by the camera setup 35, that optical 2D image or 3D surface having a virtual viewpoint similar to the viewpoint of the X-ray source 40, and is further adapted to superimpose an X-ray image acquired by the X-ray detector 31 and the optical 2D image or 3D surface in order to achieve an augmented optical/X-ray image.

According to an embodiment, a visualization method using X-ray and optical information is provided. The method comprises obtaining an X-ray image of an object with an X-ray source 40 and an X-ray detector 31; calculating an optical 2D image or a 3D surface from data delivered by a camera setup 35; and calculating an augmented 2D optical/X-ray image from the X-ray image and the 3D surface or the optical 2D image.

The methods described according to embodiments described herein may also be embodied in a computer program product, which includes computer program code that, when executed on a data processing unit, will control a diagnostic device according to embodiments described herein. This written description uses examples to disclose the invention, including the best mode, and also to enable any person skilled in the art to practice the invention, including making and using any devices or systems and performing any incorporated methods. While various specific embodiments have been disclosed in the foregoing, those skilled in the art will recognize that the spirit and scope of the claims allows for equally effective modifications. Especially, mutually non-exclusive features of the embodiments described above may be combined with each other. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A medical imaging apparatus for combined X-ray and optical visualization, comprising:
   an X-ray detector positioned above a position of a patient,
   an X-ray source positioned below a position of a patient,
   a control device,
   a camera setup comprising at least one camera adapted to deliver an optical stereoscopic or 3D image, wherein the at least one camera is adjacent to the X-ray detector above the patient,
   and wherein the control device is adapted to calculate an optical 2D image of a 3D body surface of an upper side of the patient's body from the data delivered by the camera setup, the optical 2D image including depth information of the 3D body surface, the depth information providing the optical 2D image of the 3D body surface with a virtual viewpoint below the patient's body similar to the viewpoint of the X-ray source, and is further adapted to superimpose an X-ray image acquired by the X-ray detector and the optical 2D image of the 3D body surface in order to achieve an augmented optical/X-ray image from a viewpoint below the position of the patient.

2. The apparatus of claim 1, wherein the camera setup comprises:
   a) one 3D camera, providing optical and depth information,
   b) two 3D cameras each providing optical and depth information, or
   c) two optical 2D cameras.

3. The medical imaging apparatus of claim 1, further comprising:
   a side 2D or 3D camera positioned to provide a side view on an patient to be examined, wherein the optical axis (O) of the side 2D or 3D camera is provided at an angle of about 20 to 160 degrees with respect to an axis (X) between the X-ray source and the X-ray detector,
   and wherein the control unit is adapted to calculate a 2D side image having a virtual viewpoint from a side onto the patient to be examined.

4. The medical imaging apparatus of claim 3, wherein the control unit is adapted to display the side view in form of a visual mirror located on the bicentric (BL) on the connection (C) of the X-ray source position and the center of the side 2D or 3D camera(s).

5. The medical imaging apparatus of claim 1, wherein the X-ray detector and the X-ray source are mounted to opposite sides of a C-arm.

6. The medical imaging apparatus of claim 5, wherein the X-ray detector is mounted to a side of the C-arm which is adapted to be in a position above the position of the patient to be displayed during operation.

7. The medical imaging apparatus of claim 1, wherein two 3D cameras are provided in a fixed position adjacent to and on opposite sides of the X-ray detector.

8. A visualization method using X-ray and optical information, comprising:
   a) obtaining an X-ray image with an X-ray source positioned below a position of a patient and an X-ray detector positioned above a position of a patient;
   b) calculating an optical 2D image of a 3D body surface of an upper side of the patient's body from data delivered by a camera setup comprising at least one camera, wherein the at least one camera is adjacent to the X-ray detector above the position of the patient, wherein the optical 2D image of the 3D body surface includes depth information providing the optical 2D image with a virtual viewpoint below the patient's body similar to the viewpoint of the X-ray source;
   c) superimposing the X-ray image and the optical 2D image of the 3D body surface in order to achieve an augmented 2D optical/X-ray image from a viewpoint below the position of the patient.

9. The visualization method of claim 8, further comprising:
   a) using a side 2D or 3D camera positioned to provide a side view on the patient to be examined, wherein the optical axis of the side 2D or 3D camera has an angle of about 20 to 160 degrees with respect to an axis (X) between the X-ray source and the X-ray detector,
   wherein the control unit is adapted to calculate a 2D or 3D side image having a virtual viewpoint from a side onto the patient to be examined.

10. The visualization method of claim 8, wherein the X-ray detector and the X-ray source are mounted to opposite sides of a C-arm.

11. The visualization method of claim 10, wherein the X-ray detector is mounted to a side of the C-arm which is adapted to be in a position above the position of the patient to be displayed during operation.

12. The visualization method of claim 11, wherein two 3D cameras are provided in a fixed position adjacent to and on opposite sides of the X-ray detector.

13. The medical imaging apparatus of claim 1, wherein the at least one camera and the x-ray detector have a distance of up to about 20 cm between their outer surfaces.

\* \* \* \* \*